(12) United States Patent
Claiborne et al.

(10) Patent No.: US 9,040,097 B2
(45) Date of Patent: May 26, 2015

(54) COMPOSITIONS FOR IMPROVING SKIN APPEARANCE

(71) Applicant: Inderma, Inc., Mill Valley, CA (US)

(72) Inventors: Eva Claiborne, San Rafael, CA (US); Jennifer Clara Ellis, Lawton, OK (US)

(73) Assignee: Indermica, Inc., Mill Valley, CA (US)

( * ) Notice: Subject to any disclaimer, the term of this patent is extended or adjusted under 35 U.S.C. 154(b) by 176 days.

(21) Appl. No.: 13/841,352

(22) Filed: Mar. 15, 2013

(65) Prior Publication Data

US 2014/0271524 A1    Sep. 18, 2014

(51) Int. Cl.
| | |
|---|---|
| *A61K 36/00* | (2006.01) |
| *A61K 36/87* | (2006.01) |
| *A61K 36/73* | (2006.01) |
| *A61K 8/97* | (2006.01) |
| *A61K 8/64* | (2006.01) |
| *A61K 8/66* | (2006.01) |
| *A61K 8/81* | (2006.01) |
| *A61Q 19/08* | (2006.01) |
| *A61K 8/34* | (2006.01) |
| *A61K 8/70* | (2006.01) |

(52) U.S. Cl.
CPC ... *A61K 8/97* (2013.01); *A61K 8/64* (2013.01); *A61K 8/645* (2013.01); *A61K 8/66* (2013.01); *A61K 8/8152* (2013.01); *A61Q 19/08* (2013.01); *A61K 8/345* (2013.01); *A61K 8/70* (2013.01); *A61K 8/8182* (2013.01); *A61K 8/975* (2013.01); *A61K 2800/782* (2013.01)

(58) Field of Classification Search
None
See application file for complete search history.

*Primary Examiner* — Qiuwen Mi

(74) *Attorney, Agent, or Firm* — Lee & Hayes, PLLC

(57) ABSTRACT

Compositions for reducing the appearance of wrinkles, reducing the effects of aging and/or improving the appearance of skin. The composition may include at least one fluorinated perfluorocarbon; stem cells from at least one plant species; and at least one peptide complex that reduces release of acetylcholine. Other embodied compositions include at least one collagen stimulating peptide; at least one anti-inflammatory compound; and at least one skin tightening agent.

8 Claims, No Drawings

COMPOSITIONS FOR IMPROVING SKIN APPEARANCE

BACKGROUND

Changes in skin appearance which result as a person ages can be due to many factors, such as, for example, changes in elastin and collagen. Skin appearance can also be affected by uneven pigment and changes in skin thickness, such as the thinning of the skin under and around the eyes. External or environmental factors, such as sun, weather, pollution, etc. also play a major role in skin appearance. Moreover, as life expectancies continue to rise and people continue to live longer, there is a continued increased in the demand for treatments which improve the appearance of skin and reverse the effects of aging. As the demand for such treatments continue to increase, the skin care and cosmetic market also continues to grow. However, current skin care products generally contain only the smallest effective amount of one active ingredient due to the extreme cost of available active ingredients. As such, existing skin care products only achieve minimal results over an extended period of time. Hence, there remains the need for improvement in treatments and composition which improve skin appearance by, for example, reducing the number and depth of wrinkles and other symptoms associated with aging.

BRIEF SUMMARY

This summary is provided to introduce simplified concepts of methods and compositions for reducing the number and depth of wrinkles, reducing the effects of aging and improving the appearance skin, such as skin covering the face, neck, shoulders, back or chest. Additional details of example methods and compositions are further described below in the Detailed Description. The embodiments described herein are not mutually exclusive and aspects of the various embodiments may be combined to arrive at other embodiments within the scope of the claims. This summary is not intended to identify essential features of the claimed subject matter, nor is it intended for use alone in determining the scope of the claimed subject matter.

According to an embodiment, the present invention concerns a composition comprising at least one fluorinated perfluorocarbon; stem cells from at least one plant species; at least one peptide complex that reduces release of acetylcholine, and a cosmetically acceptable carrier.

According to another embodiment, the invention concerns a composition comprising at least one collagen stimulating peptide; at least one anti-inflammatory compound; at least one skin tightening agent, and a cosmetically acceptable carrier.

DETAILED DESCRIPTION

The present disclosure relates to compositions which may be used on skin (e.g. the skin of a subject in need of such treatment) to reduce the number and depth of wrinkles and fine lines and improve the overall appearance of skin. According to an embodiment, the compositions may be used as anti-wrinkle and/or anti-aging compositions. The compositions according to the present disclosure provide a combination, or layers, of molecules/compounds which work on different skin functions. For example, according to an embodiment, the compositions include at least one compound that acts as a filler due to its weight being heavier than water so that it will fill voids caused by wrinkling, another compound helps to replenish collagen for firming of the skin, another compound acts as a hydrator offering moisturizing benefits. Combined the end results are unexpectedly faster resulting in surprisingly fuller, younger looking, and well hydrated looking skin.

According to an embodiment, the present invention concerns a composition for treating and/or reducing the appearance of wrinkles on the skin of a subject in need of such treatment. The compositions may also be used for anti-aging treatments and/or improving the appearance of a subject's skin. According to an embodiment, the composition may comprise at least one fluorinated perfluorocarbon; stem cells from at least one plant species; at least one peptide complex that reduces release of acetylcholine, and a cosmetically acceptable carrier. Moreover, one or more of the composition ingredients is present in effective amount for reducing the number and appearance of wrinkles (e.g. reducing the number and depth of wrinkles and fine lines) on skin and/or reducing the effects of aging of skin. According to certain embodiments, the composition includes stem cells from at least two plant species and/or at least two peptide complexes that reduce release of acetylcholine.

According to certain embodiments, the fluorinated perfluorocarbon may be perfluorohexane, perfluoroperhydrophenanthrene, perfluorodecalin, perfluorodimethylcyclohexane, pentafluoropropane or a combination thereof. Fluorinated perfluorocarbons are products that are fully fluorinated perfluorocarbons having a capacity to carry gases, such as Oxygen, Nitrogen and Carbon Dioxide. Fluorinated perfluorocarbons are inert materials and are not oil soluble or water-soluble and thus create a third phase in emulsions. While fluorinated perfluorocarbons contain air, they can be enriched with other gases such as Oxygen. Typical compositions of the invention contain from about 1% to about 10% by weight, from about 3% to about 7% by weight, or from about 4% to about 5% by weight, of the fluorinated perfluorocarbon. Lower concentrations may be employed for less pronounced conditions (e.g. situations where there skin has fewer and/or shallower wrinkle) and higher concentrations may be employed with more acute conditions.

According to other embodiments, the stem cells may be from a grape vine, a rose plant, an apple tree, an argan tree or a combination thereof. Stem cells from plant species are undifferentiated cells located in root meristem, shoot meristem, and vascular meristem which create all differentiated cell types and self-renew, keeping constant the number of stem cells. Examples of stem cells include, but are not limited to phytocelltec solar viti grape, phytocelltec alp rose, and phytocelltec malus domestica. Typical compositions of the invention contain from about 0.1% to about 0.5% by weight, from about 0.2% to about 0.4% by weight, or from about 2.5% to about 3.5% by weight of the stem cells. Lower concentrations may be employed for less pronounced conditions (e.g. situations where there skin has fewer and/or shallower wrinkle) and higher concentrations may be employed with more acute conditions.

According to certain embodiments, the peptide complexes that reduce release of acetylcholine may include hexapeptide-3, acetyl-hexapeptide-8, pentapeptide-3, acetyl glutamyl heptapeptide-1, heptapeptide or combinations thereof. Typical compositions of the invention contain from about 0.1% to about 5.0% by weight, from about 0.5% to about 3.0% by weight, or from about 1.0% to about 2.5% by weight of the peptide complex. Lower concentrations may be employed for less pronounced conditions (e.g. situations where there skin has fewer and/or shallower wrinkles) and higher concentrations may be employed with more acute conditions.

According to another embodiment, the composition may comprise at least one collagen stimulating peptide; at least one anti-inflammatory compound; at least one skin tightening agent, and a cosmetically acceptable carrier. Again, according to this embodiment, at least one of the composition ingredients is present in an effective amount for reducing the number and appearance of wrinkles (e.g. reducing the number and depth of wrinkles) on skin and/or reducing the effects of aging of skin. The composition according to this embodiment may also include stem cells from at least one plant species selected from the group consisting of a grape vine, a rose plant, an apple tree, an argan tree and a combination thereof as described above.

According to certain embodiments, the collagen stimulating peptide may be palmitoyl oligopeptide, palmitoyl tetrapeptide-7, or a combination thereof. Typical compositions of the invention contain from about 0.1% to about 5.0% by weight, from about 0.5% to about 3.0% by weight, or from about 1.0% to about 2.5% by weight of the collagen stimulating peptide. Lower concentrations may be employed for less pronounced conditions and higher concentrations may be employed with more acute conditions.

According to other embodiments, the anti-inflammatory compound may include hydrolyzed rice bran protein, glycine soja protein, an oxido reductase or a combination thereof. Hydrolyzed rice bran is a hydrolysate of Oryza Sativa Bran Extract derived by acid, enzyme or other method of hydrolysis. Glycine soja protein is an extract from soybeans rich in proteins, minerals and vitamins. Oxidoreductases are enzymes that reduce or block oxygen in different forms from generating free-radical damage. Typical compositions of the invention contain from about 0.1% to about 3.0% by weight, from about 0.5% to about 2.5% by weight, or from about 1.0% to about 2.0% by weight of the anti-inflammatory compound. Lower concentrations may be employed for less pronounced conditions and higher concentrations may be employed with more acute conditions.

According to certain embodiments, the skin tightening agent may include glycerin, acrylates copolymer, PVP/polycarbonyl polyglycol ester; a hydrolyzed sesame protein PG-propyl methylsilanediol; an algal extract or a combination thereof. Acrylates copolymer is polymer that includes acrylic acid and methacrylic acid monomers. Typical compositions of the invention contain from about 0.1% to about 3.0% by weight, from about 0.5% to about 2.5% by weight, or from about 1.0% to about 2.0% by weight of the skin tightening agent. Lower concentrations may be employed for less pronounced conditions and higher concentrations may be employed with more pronounced conditions.

The compositions according to the present disclosure may also include at least, capillary strengthening compounds. Suitable capillary strengthening compounds include, but are not limited to hesperidin methyl chalcone, dipeptide valyl-tryptophne, lipopeptide-GQPR and combinations thereof. Typical compositions of the invention contain from about 0.1% to about 5.0% by weight, from about 0.5% to about 3.0% by weight, or from about 1.0% to about 2.5% by weight of the capillary strengthening compounds. Lower concentrations may be employed for less pronounced conditions and higher concentrations may be employed with more pronounced conditions.

The compositions may include additional ingredients or cosmetically acceptable carriers such as, for example, surfactants, emulsifiers, foam modulators, viscosity modifiers, humectants, diluents, pH modifying agents, solvents, preservatives, thickeners, perfumes, emollients, vitamins, minerals and/or moisturizers. Exemplary surfactans include, for example Decyl Glucoside. Exemplary emulsifiers include Cetyl Alcohol, Ceteareth-20. Exemplary foam modulators include Foam Modulator: Cocamide MEA. Exemplary viscosity modifiers include Disodium EDTA and Cetyl alcohol. Exemplary humectants include hyaluronic acid. Exemplary pH modifying agents include sodium hydroxide and triethanolamine. Exemplary preservatives include phenoxyethanol, methylisothiazolinone, methylchloroisothiazolinone, and metyldibromo glutaronitrile. Exemplary thickeners include carbopol and cetyl alcohol. Exemplary emollients include apricot kernel oil, sunflower seed oil, and grape seed oil. Exemplary vitamins include tocopheryl acetate (Vitamin E), linoleic acid (Vitamin F), ascorbyl palmitate (Vitamin C), and retinyl palmitate (Vitamin A).

The compositions may be provided in the form of a serum, cream, gel, emulsion, spray, powder, lotion, ointment, soap, or stick.

Typically, topical application to skin sites is accomplished in association with a cosmetically acceptable carrier, and particularly one in which the active ingredient is soluble per se or is effectively solubilized (e.g., as an emulsion or microemulsion). Where employed, the carrier is inert in the sense of not bringing about a deactivation or oxidation of active or adjunct ingredient(s), and in the sense of not bringing about any adverse effect on the skin areas to which it is applied. For example, the compositions according to the present invention are applied in admixture with a dermatologically acceptable carrier or vehicle (e.g., as a serum, cream, gel, emulsion, spray, powder, lotion, ointment, soap, stick, or the like) so as to facilitate topical application and, in some cases, provide additional beneficial effects as might be brought about, e.g., by moisturizing of the affected skin areas. While the carrier for dermatological/cosmetic compositions can consist of a relatively simple solvent or dispersant such as water, other suitable carriers comprise a composition more conducive to topical application. In particular, a dermatological composition which will form a film or layer on the skin to which it is applied so as to localize the application and provide some resistance to washing off by immersion in water or by perspiration and/or aid in the percutaneous delivery of the active agent. Many preparations are known in the art, and include lotions containing oils and/or alcohols and emollients such as olive oil, hydrocarbon oils and waxes, silicone oils, other vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic, or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. Such compositions are referred to herein as dermally, dermatologically, or cosmetically acceptable carriers.

Generally in the practice of methods of the invention, the composition is topically applied to the skin on a subject in need of anti-wrinkle or anti-aging treatment in a predetermined or as-needed regimen either at intervals by application of a lotion or the like, it generally being the case that gradual anti-wrinkle and/or anti-aging is noted with each successive application. According to certain embodiment, the methods include applying a composition according to present invention in one form (e.g. a serum) followed by applying the same or a different composition according to the present invention in another form (e.g. a cream).

"Therapeutically effective amount" or "effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying or preventing the onset or reoccurrence of the disease or disorder or at least symptoms thereof in a subject which may be exposed to or predisposed to or may have previously suffered from a disease or disorder even though that subject does not yet experience or display symptoms of the disease or disorder.

It should be understood that the ingredients particularly mentioned above are merely examples and that some embodiments of formulations comprising the compositions of the present invention include other suitable components and agents. The compositions of the invention may be used for, among other things, pharmaceutical and cosmetic purposes and may be formulated with different ingredients according to the desired use.

EXAMPLE

Certain embodiments of the present invention are illustrated by the following Example. The present invention may, however, be embodied in many different forms and should not be construed as limited to the embodiments set forth herein; rather, these embodiments are provided so that this disclosure will be thorough and complete, and will fully convey the scope of the invention to those skilled in the art.

EXAMPLES

The following are example anti-wrinkle compositions according to the present disclosure:

Composition A: Aloe Barbadensis Leaf, Purified Water, Hydrolyzed Rice Bran Protein, Glycine Soya (Soybean) Protein, Oxido Reductases, Glycerin, Acrylates Copolymer, VP/Polycarbamyl Polyglycol Ester, Hydrolyzed Sesame Protein PG-Propyl Methylsilanediol, Ethyl hexyl Palmitate, Glyceryl Stearate, PEG-100 Stearate, Ceteayl Isononanoate, Ceteareth-20, Cetearyl Alcohol, Ceteareth-12, Cetyl Palmitate, Polyglycerylmethacylate, Propylene Glycol, Butyrospermum Parkii (Shea Butter), Malus Domestica Fruit Cell Culture Extract, Xanthan Gum, Lecithin, Phenoxyethanol, Caprylyl Glycol, Hyaluronic Acid, Carbomer, Polysorbate-20, Palmitoyl Oligopeptide, Palmitoyl Tetrapeptide-7, Disodium EDTA, Fragrance, Sodium Hydroxide, Phytonadione.

Composition B: Aloe Barbadensis Leaf, Purified Water, Perfluorohexane, Perfluoroperhydrophenanthrene, Perfluorodecalin, Perfluorodimethylcylohexane, C12-15 Alkyl Benzoate, Acetyl Hexapeptide-8, Butylene Glycol, Glycerin, Pentapeptide-3, Caprylyl Glycol, Isopropyl Palmitate, Glyceryl Stearate, Stearic Acid, Caprylic/Capric Triglyceride, Cetyl Alcohol, Caprylyl Glycol, Phenoxyethanol, Cetyl PEG/PPG-10/1 Dimethicone, Vitis Vinifera (Grape) Fruit Cell Extract, Isomalt, Lecithin, Sodium Benzoate, Rhododendron Ferrugineum Leaf Cell Culture Extract, Lactic Acid, Hyaluronic Acid, Malus Domestica Fruit Cell Culture Extract, Xanthan Gum, Phenoxyethanol, Carbomer, Laureth-4, Fragrance, Triethanolamine.

The following is a prophetic example method of using a composition according to the present disclosure.

One or both of the compositions described above is/are topically applied to the face of a subject in need of anti-wrinkle or anti-aging treatment. After the composition(s) is/are applied, the subject's face is then massaged for about 15 to 20 minutes or until the temperature of the subject's facial skin increases about 1.0 to 1.5° F. After massaging with the composition(s), the subject will experience a reduction in fine lines and wrinkle depth. Moreover, the application and massage treatments are repeated over a course of days or weeks.

While applicant's disclosure has been provided with reference to specific embodiments above, it will be understood that modifications and alterations in the embodiments disclosed may be made by those practiced in the art without departing from the spirit and scope of the invention. All such modifications and alterations are intended to be covered.

We claim:

1. A composition comprising:
   a. at least one fluorinated perfluorocarbon;
   b. stem cells from at least one plant species;
   c. at least one peptide complex that reduces release of acetylcholine; and
   d. a cosmetically acceptable carrier.

2. The composition according to claim 1, wherein said fluorinated perfluorocarbon is perfluorohexane, perfluoroperhydrophenanthrene, perfluorodecalin, perfluorodimethylcyclohexane, pentafluoropropane or a combination thereof.

3. The composition according to claim 1, wherein said stem cells are from a grape vine, a rose plant, an apple tree, an argan tree or a combination thereof.

4. The composition according to claim 1, wherein said peptide complex is hexapeptide-3, acetyl-hexapeptide-8, pentapeptide-3, acetyl glutamyl heptapeptide-1, heptapeptide.

5. The composition according to claim 1, comprising stem cells from at least two plant species, at least two peptide complexes that reduce release of acetylcholine or both.

6. A composition according to claim 1, wherein the cosmetically acceptable carrier includes one more of a surfactant, an emulsifier, a foam modulator, a viscosity modifier, a humectant, a diluent, a filler, a pH modifying agent, a colorant, a solvent, a preservative, a thickener, a perfume, an emollients, a vitamin, a mineral, a moisturizer, or a combination thereof.

7. The composition of claim 1, wherein said composition is provided in a serum, cream, gel, emulsion, spray, powder, lotion, ointment, soap, or stick.

8. A method for reducing the appearance of wrinkles on skin comprising applying the composition according to claim 1 to a portion of skin.

* * * * *